US011267833B2

(12) United States Patent
Chikkali et al.

(10) Patent No.: US 11,267,833 B2
(45) Date of Patent: Mar. 8, 2022

(54) COMPOUNDS AND PROCESS FOR PREPARATION OF THE SAME FROM CASHEW NUT SHELL LIQUID (CNSL)

(71) Applicant: Council of Scientific & Industrial Research, New Delhi (IN)

(72) Inventors: Samir Hujur Chikkali, Pune (IN); Swechchha Pandey, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 16/857,501

(22) Filed: Apr. 24, 2020

(65) Prior Publication Data

US 2020/0247834 A1 Aug. 6, 2020

Related U.S. Application Data

(62) Division of application No. 16/339,828, filed as application No. PCT/IN2017/050454 on Oct. 6, 2017, now Pat. No. 10,683,317.

(30) Foreign Application Priority Data

Oct. 7, 2016 (IN) ............................ 201611034415

(51) Int. Cl.

*C07C 37/00* (2006.01)
*C07F 15/00* (2006.01)
*C07C 47/277* (2006.01)
*C07C 45/50* (2006.01)
*C07C 47/27* (2006.01)

(52) U.S. Cl.

CPC ............ *C07F 15/00* (2013.01); *C07C 37/003* (2013.01); *C07C 37/004* (2013.01); *C07C 45/50* (2013.01); *C07C 47/27* (2013.01); *C07C 47/277* (2013.01)

(58) Field of Classification Search

CPC ..... C07F 15/00; C07C 37/003; C07C 37/004; C07C 45/50

See application file for complete search history.

(56) References Cited

U.S. PATENT DOCUMENTS

| | | | | |
|---|---|---|---|---|
| 2,284,369 | A * | 5/1942 | Caplan .................... | C07C 41/16 568/780 |
| 5,202,355 | A | 4/1993 | Nakatsu | |
| 7,825,284 | B2 * | 11/2010 | Sato ...................... | C07C 37/685 568/763 |
| 10,683,317 | B2 * | 6/2020 | Chikkali ................ | C07C 45/50 |
| 2002/0004576 | A1 | 1/2002 | Khan et al. | |
| 2009/0068126 | A1 | 3/2009 | Romeiro et al. | |
| 2012/0129963 | A1 * | 5/2012 | Benedetti .............. | C07C 37/115 521/97 |

OTHER PUBLICATIONS

Hawley's Condensed Chemical Dictionary, pp. 38-40 (16th ed., 2016, R.J. Larrañaga ed.) (Year: 2016).*
C. Feitosa et al. Quimica Nova, 41-44 (2007) (Year: 2007).*
CAS Abstract and Indexed Compound C. Feitosa et al. Quimica Nova, 41-44 (2007) (Year: 2007).*
CAS Abstract and Indexed Compound, E. Benedetti et al., US 2012/0129963 (2012) (Year: 2012).*
S. Pandey et al., 9 ChemCatChem, 3997-4004 (2017) (Year: 2017).*
Abstract S. Pandey et al., 9 ChemCatChem, 3997-4004 (Jun. 16, 2017) (Year: 2017).*
Y. Liu et al., 17 Journal of the Brazilian Chemical Society, 527-532 (2006) (Year: 2006).*
CAS Abstract and Indexed Compound Y. Liu et al., 17 Journal of the Brazilian Chemical Society, 527-532 (2006) (Year: 2006).*
F. Gelin et al., 27 Journal of Analytical and Applied Pyrolysis, 155-168 (1993) (Year: 1993).*
K. Franke et al., 67 Planta Med, 477-479 (2001) (Year: 2001).*
Backer et al., "The Structure of Pelandjauic Acid (La Structure De L'acide Pe̅landjauíque)", Proc. Acad. Sci. Amsterdam Acad. Sci. Amsterdam; vol. 60, Issue 9, https://doi.org/10.1002/recl. 19410600907, 1941, pp. 678-688.
Behr et al, "Isomerizing hydroformylation of fatty acid esters: Formation of -aldehydes", Eur. J. Lipid Sci. Technol., vol. 107, 2005, pp. 213-219.
Franke et al., "Cardanols from Leaves of Rhus thyrsiflora". Planta Medica, vol. 67, 2001, pp. 477-479.
Julis et al., "Selective ethenolysis and oestrogenicity of compounds from cashew nut shell liquid", Green Chemistry, vol. 16, 2014, pp. 2846-2856.
Pandey et al., "Highly Regioselective Isomerizing Hydroformylation of Long-Chain Internal Olefins Catalyzed by a Rhodium Bis(Phosphite) Complex", Chemcatchem, vol. 7, No. 21, 2015, pp. 3468-3471.
Perdriau et al., "Selective Conversion of Polyenes to Monoenes by RuCI3-Catalyzed Transfer Hydrogenation: The Case of Cashew Nutshell Liquid", Chemsuschem, vol. 5, No. 12, 2012, pp. 2427-2434.
Takahashi et al., "Tandem Hydroformylation/Hydrogenation of Alkenes to Normal Alcohols Using Rh/Ru Dual Catalyst or Ru Single Component Catalyst", Journal of the American Chemical Society, 2012, pp. 18746-18757.
Viches-Herrera et al., "Hydroformylation Tandem Reactions", ACS Catalysis, vol. 4, 2014, pp. 1706-1724.

(Continued)

*Primary Examiner* — Alexander R Pagano
(74) *Attorney, Agent, or Firm* — Dinsmore & Shohl, LLP

(57) ABSTRACT

The present invention relates to isomerizing hydroformylation of plant oils to feedstock chemicals and monomers. More particularly, the present invention relates to compound of formula (I) and process for preparation thereof using isomerizing functionalization of cashew nut shell liquid (CNSL).

Formula (I)

OR

E

2 Claims, 7 Drawing Sheets

(56) References Cited

OTHER PUBLICATIONS

Yuki et al., "Tandem Isomerization/Hydroformylation/Hydrogenation of Internal Alkenes to n-Alcohols Using Rh/Ru Dual- or Ternary-Catalyst Systems", Journal of the American Chemical Society, vol. 135, 2013, pp. 17393-17400.

International Search Report and Written Opinion, completed Nov. 28, 2017, pertaining to PCT/IN2017/050454, filed Oct. 6, 2017.

* cited by examiner

COMPOUNDS AND PROCESS FOR PREPARATION OF THE SAME FROM CASHEW NUT SHELL LIQUID (CNSL)

CROSS-REFERENCE TO RELATED APPLICATIONS

This application is a divisional of U.S. patent application Ser. No. 16/339,828, filed Apr. 5, 2019, which is a is a national stage application, filed under 35 U.S.C. § 371, of International Patent Application No. PCT/IN2017/050454, filed on Oct. 6, 2017, which claims priority to IN 201611034415, filed Oct. 7, 2016, which is incorporated by reference herein in its entirety.

FIELD OF THE INVENTION

The present invention relates to isomerizing hydroformylation of plant oils to feedstock chemicals and monomers. More particularly, the present invention relates to compound of formula (I) and process for the preparation thereof using isomerizing functionalization of cashew nut shell liquid (CNSL).

BACKGROUND OF THE INVENTION

Today's chemical world rely mainly on fossils fuel resources. However, due to depleting fossils fuel resources and ever increasing emission of greenhouse gases there is a strong motivation to substitute fossils fuel resources with renewable resources. Currently, in the era of petroleum economy, there exists an intense focus on the production of transportation fuels and other platform chemicals from biomass. This focus can be ascribed to a desire to significantly lower the emission of greenhouse gases thereby minimizing global warming and also to renounce dependence on fossils fuels.

Plant oil derived fatty acids can be a suitable alternative as they have characteristic long methylene sequence with an internal double bond. This internal double bond provides an excellent opportunity to further functionalize the plant oil to useful chemicals and materials. Therefore it has been a long cherished dream of organometallic chemists to isomerize the double bond to terminal position and functionalize it selectively. However isomerization of internal double bond to terminal olefins is thermodynamically unfavorable which makes the terminal functionalization of plant oil a challenging transformation. A very few attempts have been made to address this bottle-neck in the past. Isomerizing hydroformylation of fatty acid methyl esters (FAMEs) was first reported by Behr et al. and very limited success was achieved (26% terminal aldehyde). The conversion is slightly improved in case of isomerizing hydroboration (45%). Isomerizing metathesis is of significant importance and is successfully up scaled and various products such as candle waxes, cosmetics etc. are claimed to be produced by this transformation. The most successful example is isomerizing alkoxycarbonylation (>95% terminal selectivity) which was first introduced by Cole-Hamilton and later developed by Mecking et al. The mechanism of this particular process has been investigated by Mecking and coworkers.

India is the second largest producer of Cashew Nut Shell Liquid (CNSL) with an annual production of more than 20,000 tones. CNSL is a versatile byproduct of cashew industry and is a renewable and inexpensive resource. It is obtained from spongy mesocarp of cashew nut shell. The CNSL can be obtained by extraction in hot oil; liquid extraction (solvents); mechanical expulsion from the shells or by vacuum distillation. The variability of composition depends of extraction method but in general, the composition of natural CNSL is a mixture of anacardic acid, cardanol, cardol and 2-methyl-cardol in smaller quantities. Decarboxylation of anacardic acid at 140° C. followed by vacuum distillation results in cardanol in pure form. The relative composition of monoene, diene and triene in cardanol is established with HPLC. Diene and triene can selectively be hydrogenated to monoene when cardanol is subjected to selective hydrogenation in presence of $RuCl_3$ and isopropanol.

Article titled "Tandem hydroformylation/hydrogenation of alkenes to normal alcohols using Rh/Ru dual catalyst or Ru single component catalyst" by Kohei Takahashi et al. published in Journal of the American Chemical Society, 2012, 134, pp 18746-18757 reports detailed investigation about Ru-catalyzed hydrogenation of undecanal under $H_2$/CO pressure clarified different kinetics from the hydrogenation under $H_2$ and gave a clue to design more active hydrogenation catalysts under $H_2$/CO atmosphere. The solely Ru-catalyzed normal selective hydroformylation/hydrogenation is also reported.

Article titled "Tandem isomerization/hydroformylation/hydrogenation of internal alkenes to N-alcohols using Rh/Ru dual- or ternary-catalyst systems" by Yamato Yuki et al. published in *Journal of the American Chemical Society,* 2013, 135, 17393-17400 reports A one-pot three-step reaction, isomerization/hydroformylation/hydrogenation of internal alkenes to alcohols, was accomplished by employing a Rh/Ru dual-catalyst system. By using a combination of $Rh(acac)(CO)_2$/bisphosphite and Shvo's catalyst, (Z)-2-tridecene was converted to 1-tetradecanol in 83% yield with high normal/iso selectivity (n/i=12). The method was applicable to other internal alkenes, including functionalized alkenes, such as an alkenol and an alkenoate.

Article titled "Isomerizing hydroformylation of fatty acid esters: Formation of co-aldehydes" by Arno Behr et al. published in *European Journal of Lipid Science and Technology,* 107 (2005) 213-219 reports The isomerizing hydroformylation of fatty acid esters to oleochemicals with an additional o-standing aldehyde group can be performed at a relatively low temperature and a synthesis gas pressure of 20 bar. In the case of oleic acid ester, the best yield of linear aldehyde is 26%; in the case of linoleic acid ester, it is 34%. For both fatty compounds, a strong hydrogenation side reaction is observed, which can be explained by a steering effect of the ester group. The ester function of the fatty compounds makes hydroformylation in the surrounding area of this group impossible. Reactions with the model substances ethyl crotonate and ethyl sorbate showed that hydrogenation predominates, leading to the corresponding saturated compounds.

Article titled "Selective ethenolysis and oestrogenicity of compounds from cashew nut shell liquid" by Jennifer Julis et al. published in *Green Chem.,* 2014, 16,2846 reports the ethenolysis of cardanol (2), a waste product from cashew kernel production, was carried out using a variety of metathesis catalysts. Surprisingly, the best activities and selectivities could be observed with ruthenium based 1st generation type catalysts converting cardanol (2) almost completely to the corresponding 1-octene (6) and 3-non-8-enylphenol (4), a potential detergent precursor. Detailed investigation of the reaction system showed that the high activity and selectivity were due to a combination of ethenolysis and internal self-metathesis of the unsaturated cardanol mixture, 2. Self-metathesis of cardanol (2) containing three double bonds led to the formation of 3-non-8-enylphenol (4) and 1,4-cyclohexadiene (7). The latter was crucial for a high selectivity and activity in the ethenolysis, not only of cardanol (2), but also of other substrates like methyl oleate (10) when using ruthenium based 1st generation catalysts. The endocrine disrupting properties of 3-nonylphenol and related compounds are compared.

Article titled "Isomerization-Hydroformylation Tandem Reactions" by Marcelo Vilches-Herrera et al. published in *ACS Catalysis,* 2014, 4, 1706-1724 reports Rhodium-Catalyzed isomerization of aldehydes. Conversion and product distribution in the Hydroformylation of isomeric C8-olefins with an unmodified Cobalt catalyst.

Developing similar terminal selectivity in a one pot isomerizing hydroformylation reaction will be of utmost significance, as it would provide a powerful tool for heterofunctionalization of plant oils along with complete feedstock utilization. Therefore, there is need to develop isomerizing hydroformylation of plant oils using metal precursor.

OBJECTIVES OF THE INVENTION

Main objective of the present invention is to provide a compound of formula (I).

Another objective of the present invention is to provide a process for the preparation of said compound of formula (I) using isomerizing functionalization of cashew nut shell liquid (CNSL).

Still another objective of the present invention is to provide use of said compound of formula (I) as monomer for the preparation of polymer or copolymer.

Yet another objective of the present invention is to provide a catalyst of formula (II).

SUMMARY OF THE INVENTION

Accordingly, the present invention provides a compound of formula (I);

Formula (I)

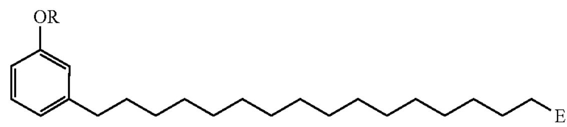

wherein;

R is selected from hydrogen or alkyl;

E is selected from hydrogen, alkyl, aldehyde, alcohol, acid and amino.

In preferred embodiment, said compound of formula (I) is selected from 16-3(hydroxyphenyl) hexadecanal (P1) and is 16-(3-methoxyphenyl) hexadecanal (P2).

In an embodiment, the present invention provides a process for the preparation of compound of formula (I) comprising the steps of:

a) adding catalyst to a solution of cardanol in solvent followed by refluxing the reaction mixture for the period in the range of 16 to 18 hrs at temperature in the range of 85 to 90° C. to obtain monoene;
b) adding metal precursor and ligand to the mixture of monoene of step (a) in suitable solvent followed by pressurizing and heating the reaction mixture at temperature in the range of 100 to 125° C. for the period in the range of 16 to 48 hours to afford corresponding aldehyde compound of formula (I) and
c) optionally reacting monoene of step (a) and potassium carbonate in solvent followed by adding alkyl iodide to the mixture and refluxed for the period in the range of 4 to 6 hrs at temperature in the range of 56 to 60° C. to afford alkyl-protected monoene.

In preferred embodiment, said catalyst of step (a) is Ruthenium(III) chloride ($RuCl_3$).

In another preferred embodiment, said solvent of step (a) is selected from isopropanol, methanol, ethanol, isopropanol and tert-butanol.

In still another preferred embodiment, said metal precursor is (Acetylacetonato)dicarbonylrhodium(I) ($[Rh(acac)(CO)_2]$).

In yet another preferred embodiment, said ligand is selected from 1,2-Bis(di-tert-butylphosphinomethyl)benzene (1,2-DTBPMB), 1,3-phenylene tetra(naphthalen-1-yl) bis(phosphite) (L2), Xantphos, 2,2'-Bis(diphenylphosphino)-1,1'-binaphthalene (BINAP).

In still yet another preferred embodiment, said solvent of step (b) is selected from toluene, p-xylene, Mesitylene, N-Methyl-2-pyrrolidone (NMP), Dimethoxyethane (DME), 1,4-dioxane.

In still yet another preferred embodiment, said solvent of step (c) is selected from acetone, methanol, and ethanol.

In still yet another preferred embodiment, said alkyl iodide is methyl iodide.

In still yet another preferred embodiment, said alkyl-protected monoene is selected from methyl-protected monoene, ethyl-protected monoene.

In still yet another preferred embodiment, said monoene is selected from (E)-3-(pentadec-8-1-yl)phenol (S1) and (E)-1-methoxy-3-(pentadec-8-en-1-yl) benzene (S1-Me).

In still yet another preferred embodiment, said compound of formula (I) is used for the preparation of polymer or copolymer.

In another embodiment, a compound of formula (II) for isomerizing hydroformulation of monoene;

Formula (II)

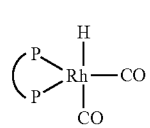

wherein;

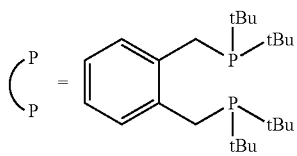

DETAILED DESCRIPTION OF THE INVENTION

Figure 1:
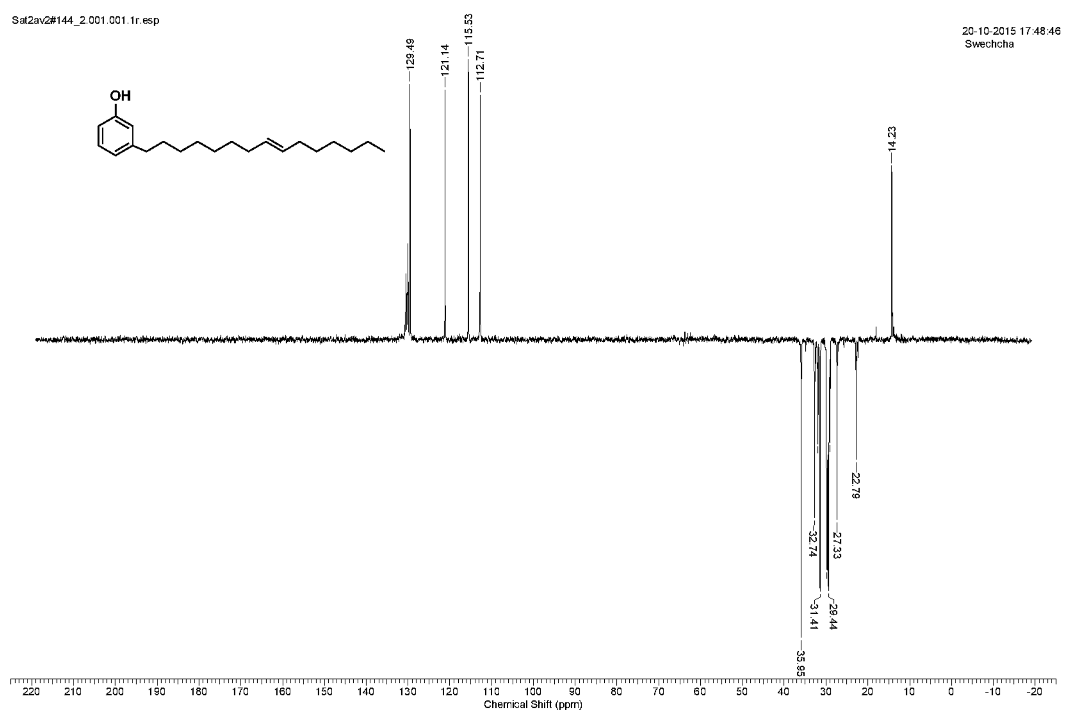
FIG. 1: 13C (DEPT) NMR spectrum of monoene.

The invention will now be described in detail in connection with certain preferred and optional embodiments, so that various aspects thereof may be more fully understood and appreciated.

The present invention provides a compound of formula (I);

Formula (I)

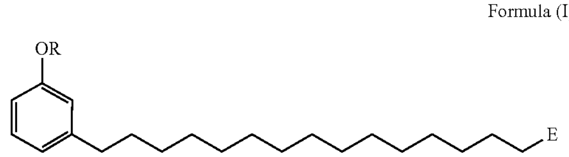

wherein;

R is selected from hydrogen or alkyl;

E is selected from hydrogen, alkyl, aldehyde, alcohol, acid and amino.

In preferred embodiment, said compound of formula (I) is selected from 16-3(hydroxyphenyl) hexadecanal (P1) and is 16-(3-methoxyphenyl) hexadecanal (P2).

In an embodiment, the present invention provides a process for the preparation of compound of formula (I) comprising the steps of:

a) Selective reduction of cardanol to monoene;

b) Isomerizing hydroformylation of monoene of step (I).

In preferred embodiment, the present invention provides a process for the preparation of compound of formula (I) comprising the steps of:

a) adding catalyst to a solution of cardanol in solvent followed by refluxing the reaction mixture for the period in the range of 16 to 18 hrs at temperature in the range of 85 to 90° C. to obtain monoene;

b) adding metal precursor and ligand to the mixture of monoene of step (a) in suitable solvent followed by pressurizing and heating the reaction mixture at temperature in the range of 100 to 125° C. for the period in the range of 16 to 48 hours to afford corresponding aldehyde compound of formula (I) and c) optionally reacting monoene of step (a) and potassium carbonate in solvent followed by adding alkyl iodide to the mixture and refluxed for the period in the range of 4 to 6 hrs at temperature in the range of 56 to 60° C. to afford alkyl-protected monoene.

In preferred embodiment, said catalyst of step (a) is Ruthenium(III) chloride ($RuCl_3$).

In another preferred embodiment, said solvent of step (a) is selected from isopropanol, methanol, ethanol, isopropanol and tert-butanol.

In still another preferred embodiment, said metal precursor is (Acetylacetonato)dicarbonylrhodium(I) ([Rh(acac)$(CO)_2$]).

In yet another preferred embodiment, said ligand is selected from 1,2-Bis(di-tert-butylphosphinomethyl)benzene (1,2-DTBPMB), 1,3-phenylene tetra(naphthalen-1-yl) bis(phosphite)-(L2), Xantphos, 2,2'-Bis(diphenylphosphino)-1,1'-binaphthalene (BINAP).

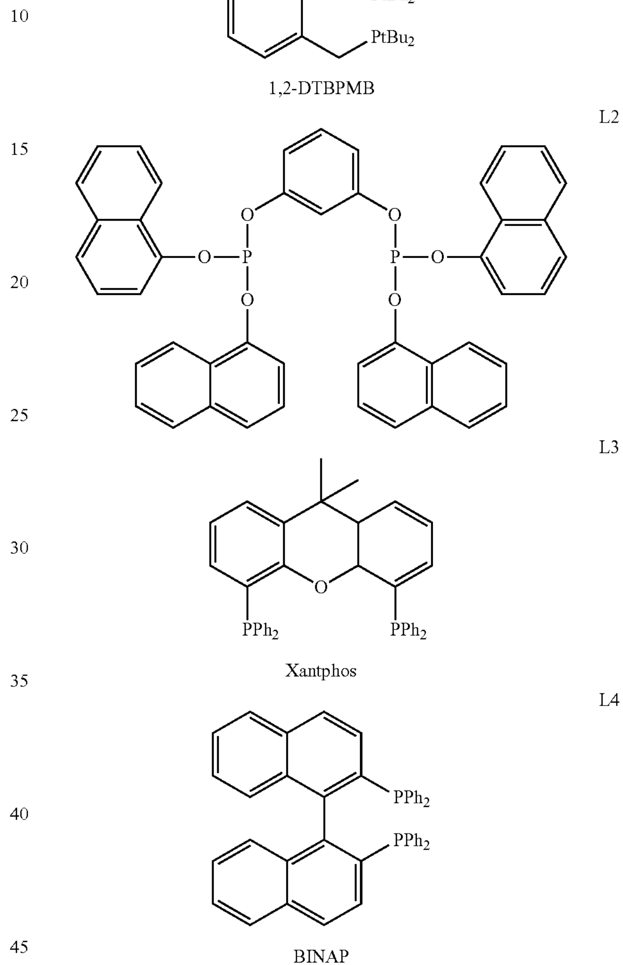

In still yet another preferred embodiment, said solvent of step (b) is selected from toluene, p-xylene, Mesitylene, N-Methyl-2-pyrrolidone (NMP), Dimethoxyethane (DME), 1,4-dioxane.

In still yet another preferred embodiment, said solvent of step (c) is selected from acetone, methanol, and ethanol.

In still yet another preferred embodiment, said alkyl iodide is methyl iodide.

In still yet another preferred embodiment, said alkyl-protected monoene is selected from methyl-protected monoene, ethyl-protected monoene.

In still yet another preferred embodiment, said monoene is selected from (E)-3-(pentadec-8-1-yl)phenol (S1) and (E)-1-methoxy-3-(pentadec-8-en-1-yl) benzene (S2).

In still yet another preferred embodiment, said compound of formula (I) is used for the preparation of polymer or copolymer.

The compound of formula (I) may be used as an AB type monomer and its polymerization will give a polymer that will have a phenyl ring in the polymer chain. As a result of the obtained polymer will have improved fire retardant properties than the polymer obtained from other plant oils.
The process for the preparation of compound of formula (I) is shown in scheme 1 below.
Scheme 1
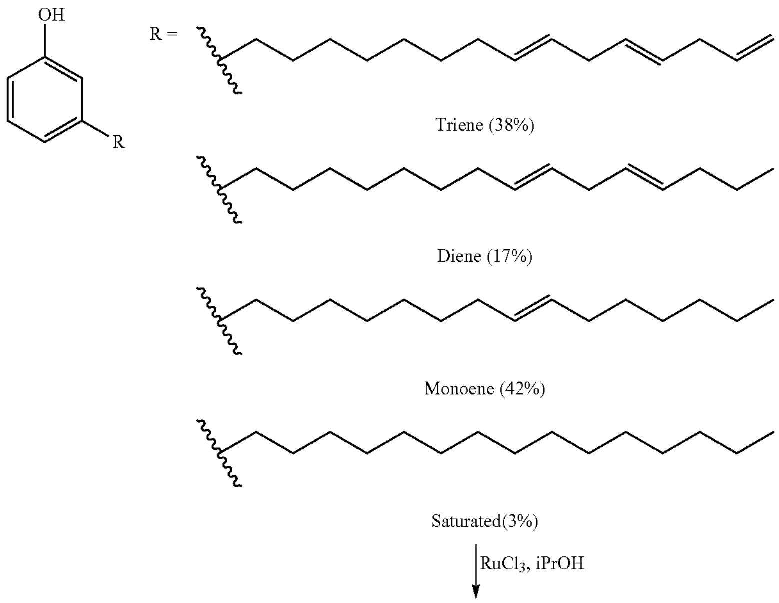
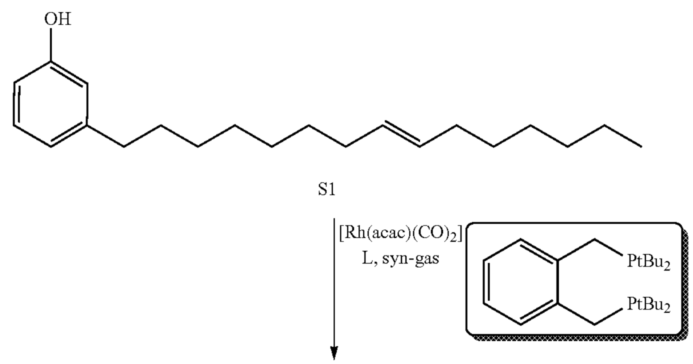
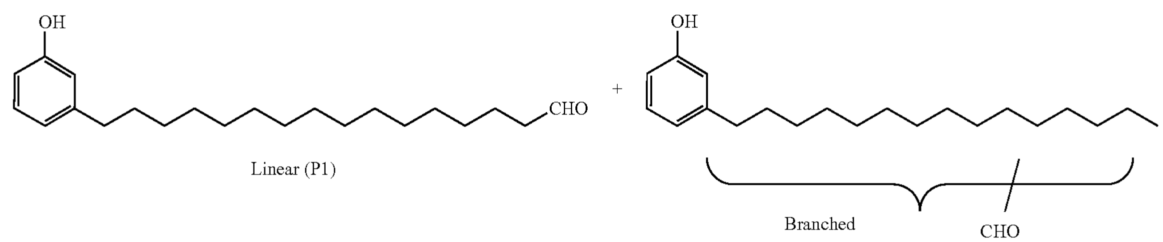

In another embodiment, the present invention provides an efficient process for isomerizing functionalization of cashew nut shell liquid for the first time and an unprecedented terminal selectivity of 33% is obtained in case of monoene S1. The terminal selectivity is even better (50%) when free —OH group of monoene is protected in the form of methyl (S2).

In still another embodiment, the present invention provides a catalyst of formula (II);

Formula (II)

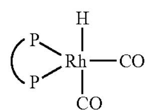

wherein;

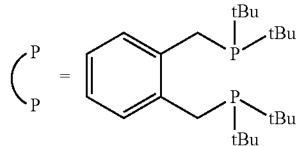

In yet another embodiment, the present invention provides isomerizing hydroformylation of CNSL-cardanol.

Scheme 2 shows isomerizing hydroformylation of cardanol and possible products.

Scheme 2

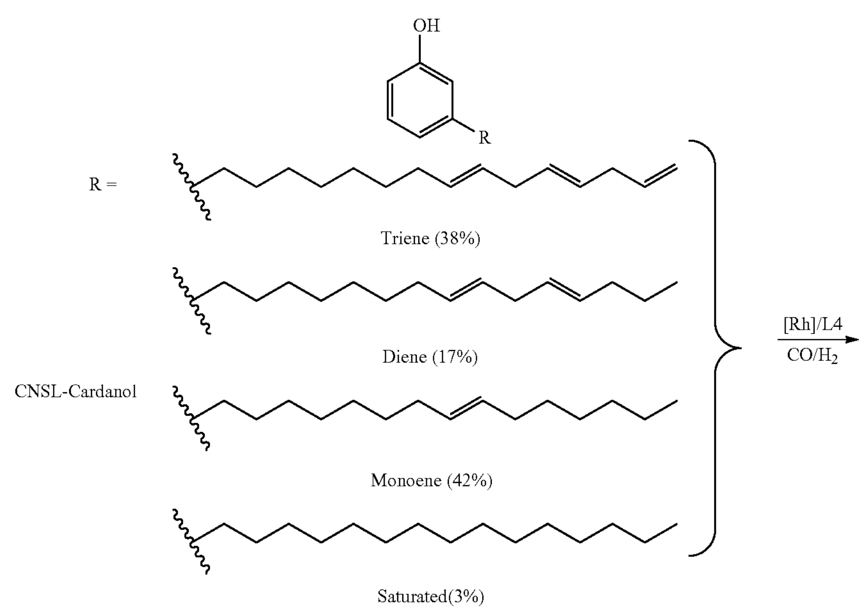

-continued

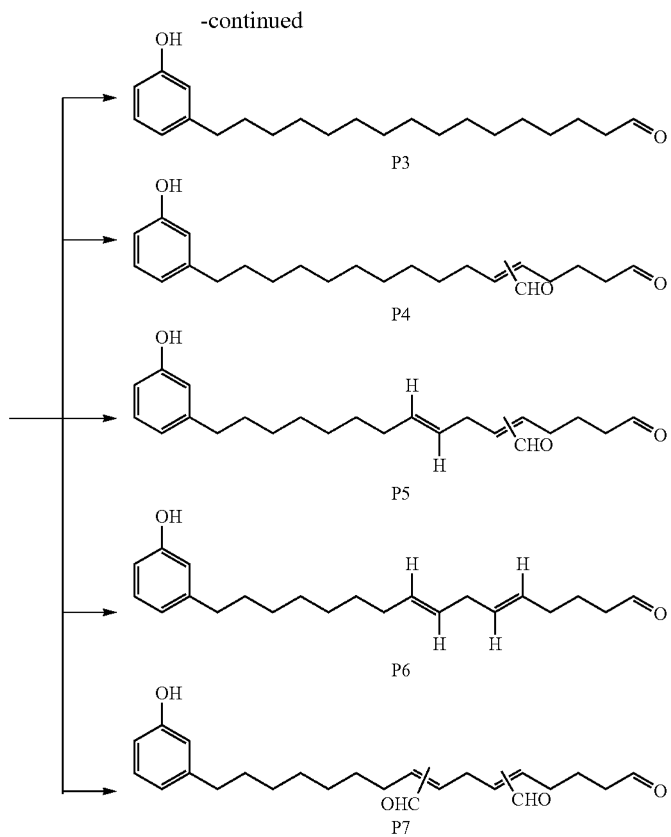

Isomerizing hydroformylation of crude cardanol proved to be highly selective than that of pure monoene. The improved terminal selectivity can be explained based on the fact that the CNSL-cardanol mixture consists of a triene component with readily available terminal double bond. Thus, the hydroformylation of this terminal double bond adds up to the isomerizing hydroformylation of internal double bonds and overall terminal selectivity is improved. However, due to presence of multiple double bonds in the starting material, formation of dialdehyde and trialdehyde along with monoaldehyde is highly favorable. Obtained regio-selectivities are further confirmed using HPLC analysis. HPLC analyses are performed on Agilent 1260 infinity series instrument using ACN+water+formic acid (93+2+5) as eluents, flow rate 0.5 ml/min., column C18, 5 μm, 4.6*250 mm, $\lambda_{max}$=273 nm, P6: $R_t$=6.3 minutes.

In still yet another embodiment, the present invention provides isomerizing hydroformylation of S1, S2, S3 and S4 to P1 and P6, and subsequent hydrogenation of P6 to P8 as shown in Scheme 3.

Scheme 3

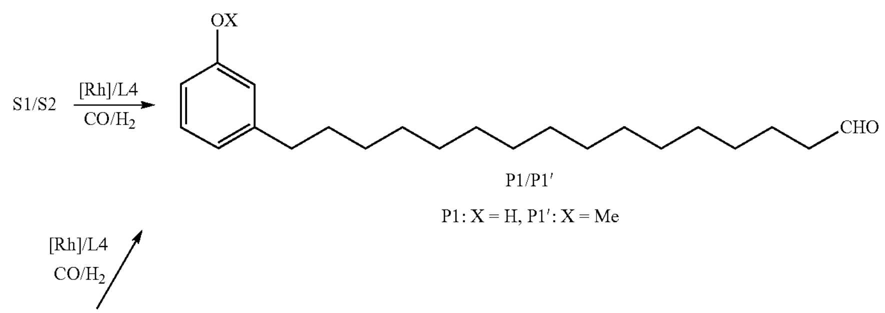

-continued

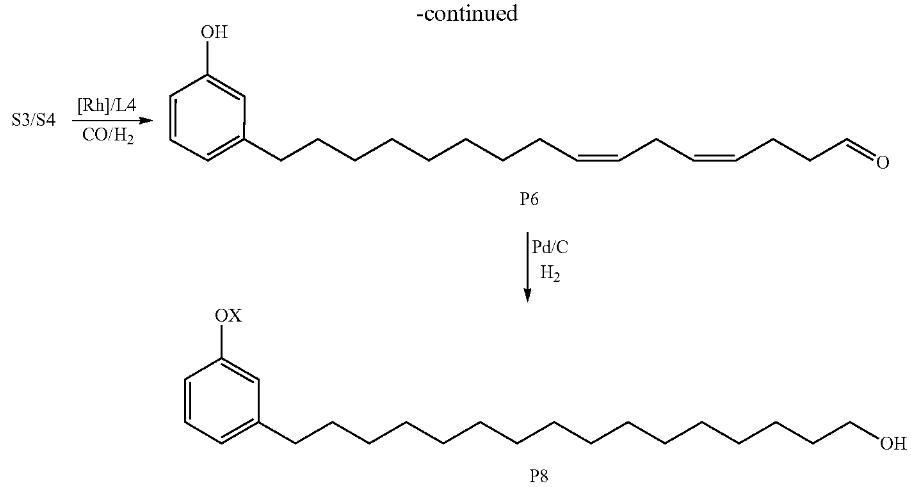

FIG. 1 depicts DEPT spectrum of monoene.

Figure 2:
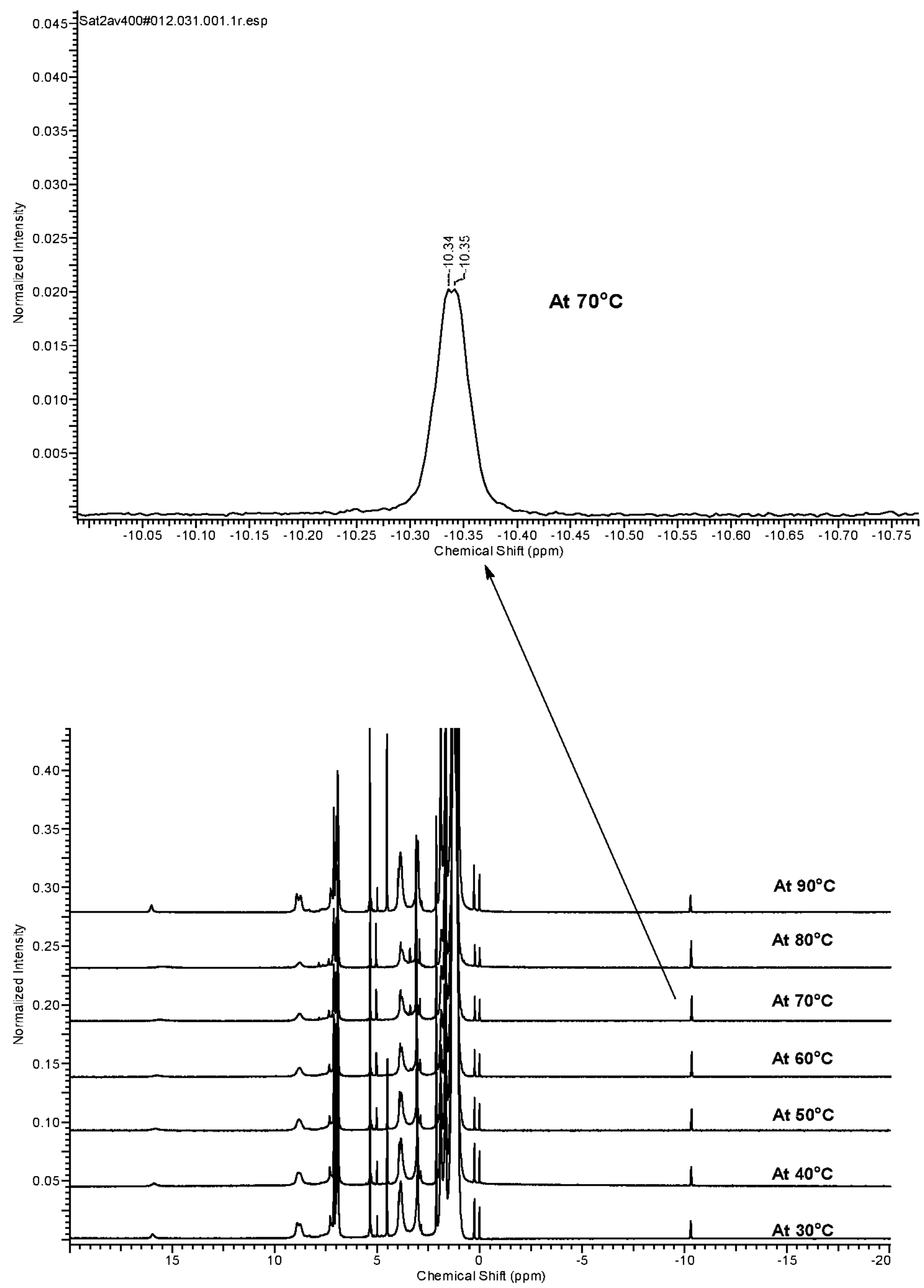
FIG. 2: High pressure $^{1}H$ NMR spectrum of rhodium complex in formula (II) at higher temperature.

FIG. 2 depicts high pressure $^1$H NMR spectrum of rhodium complex in formula (II) at higher temperature.

Figure 3:
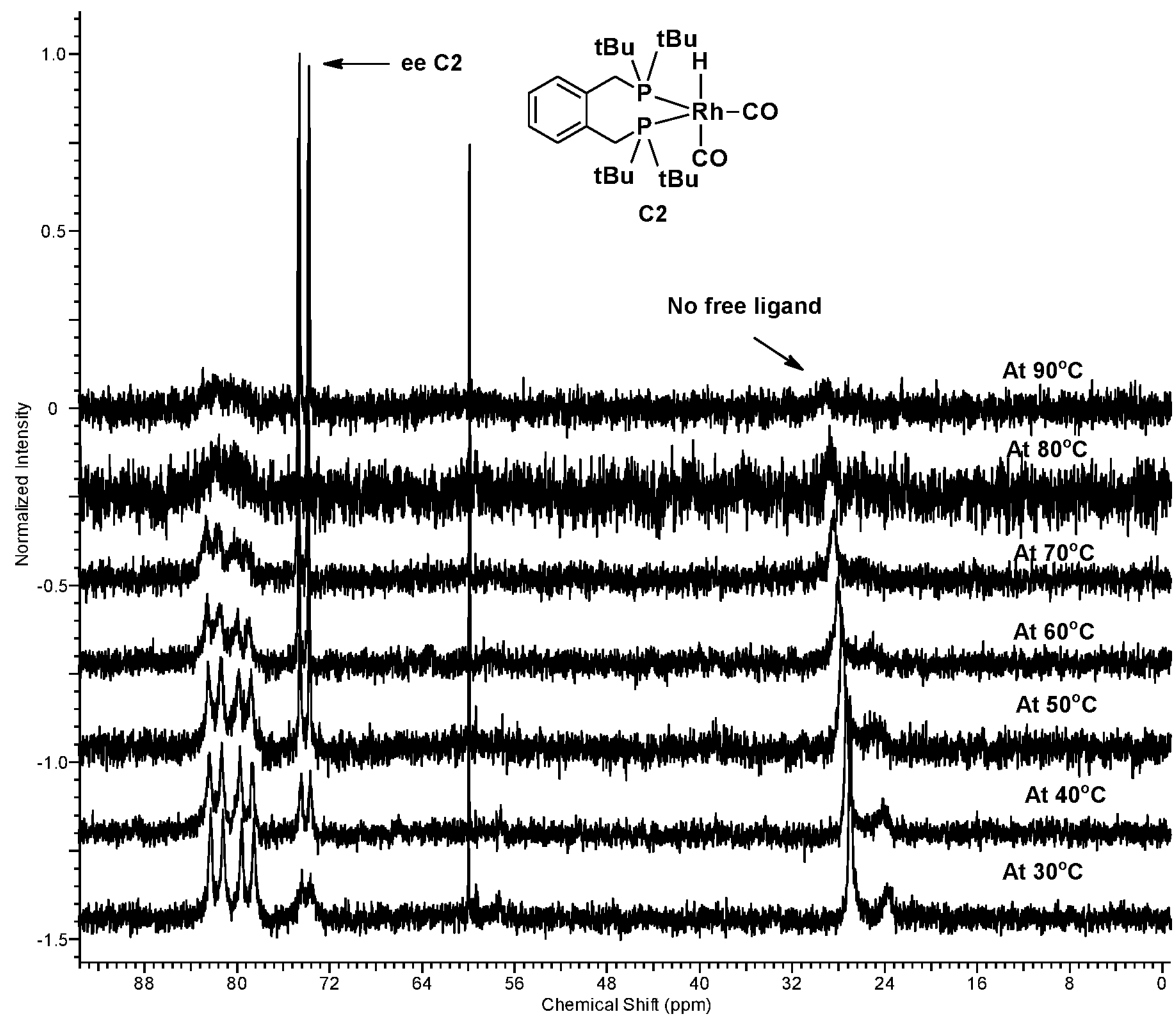
FIG. 3: High pressure $^{31}P$ NMR spectrum of rhodium complex in formula (II) at higher temperature.

FIG. 3 depicts high pressure $^{31}$P NMR spectrum of rhodium complex in formula (II) at higher temperature.

Figure 4:
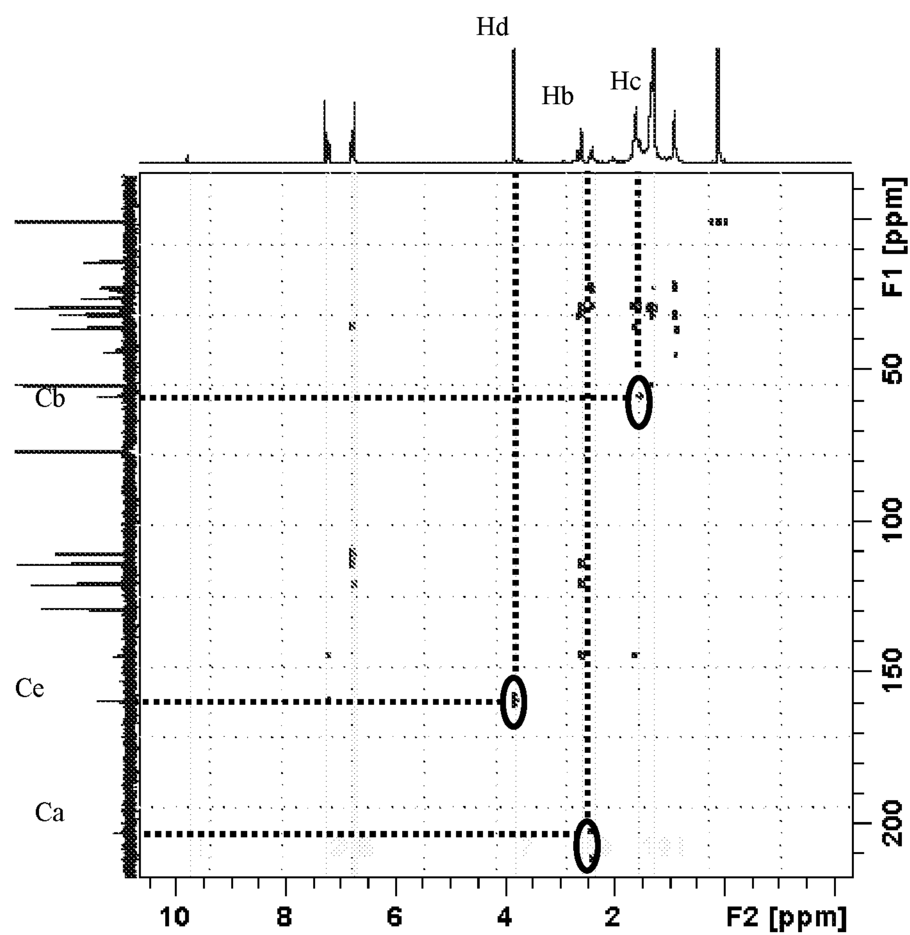
FIG. 4: A long range C—H correlation (HMBC) spectrum of linear aldehyde (P1') in $CDCl_3$

FIG. 4 depicts a long range C—H correlation (HMBC) spectrum of linear aldehyde (P1') in $CDCl_3$.

Figure 5:
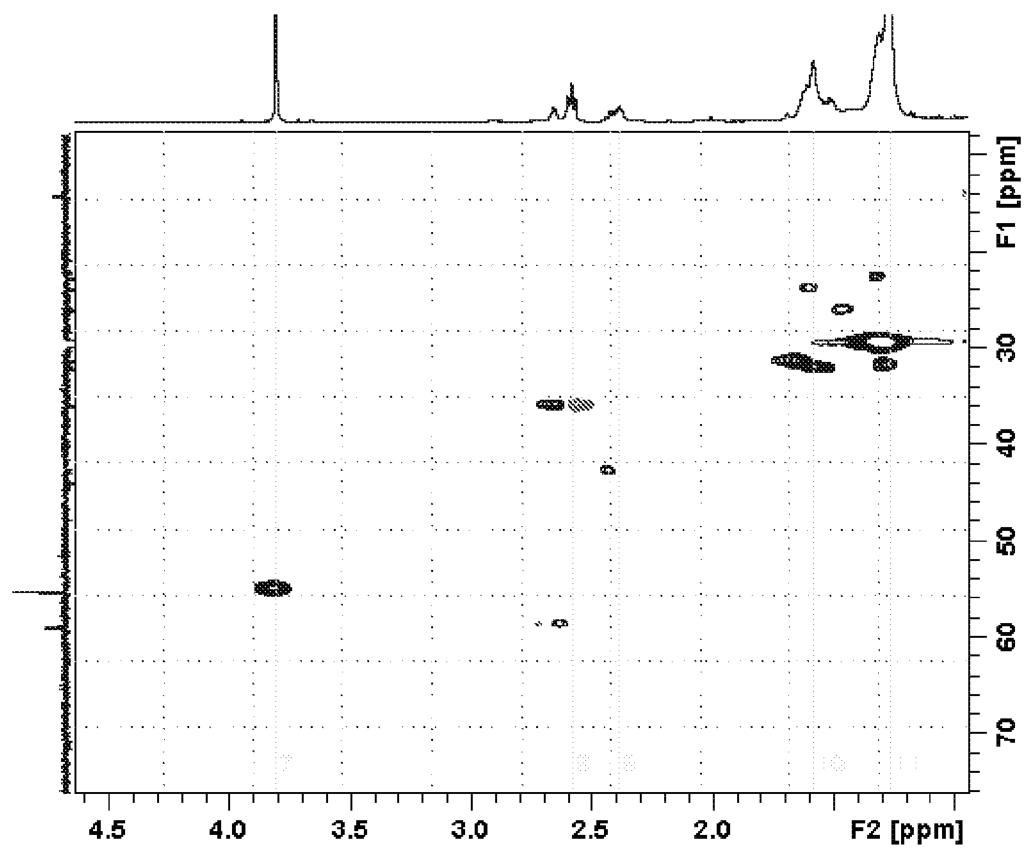
FIG. 5: Direct C—H correlation (HSQC) spectrum of linear aldehyde (P1') in $CDCl_3$

FIG. 5 depicts direct C—H correlation (HSQC) spectrum of linear aldehyde (P1') in $CDCl_3$.

Figure 6:
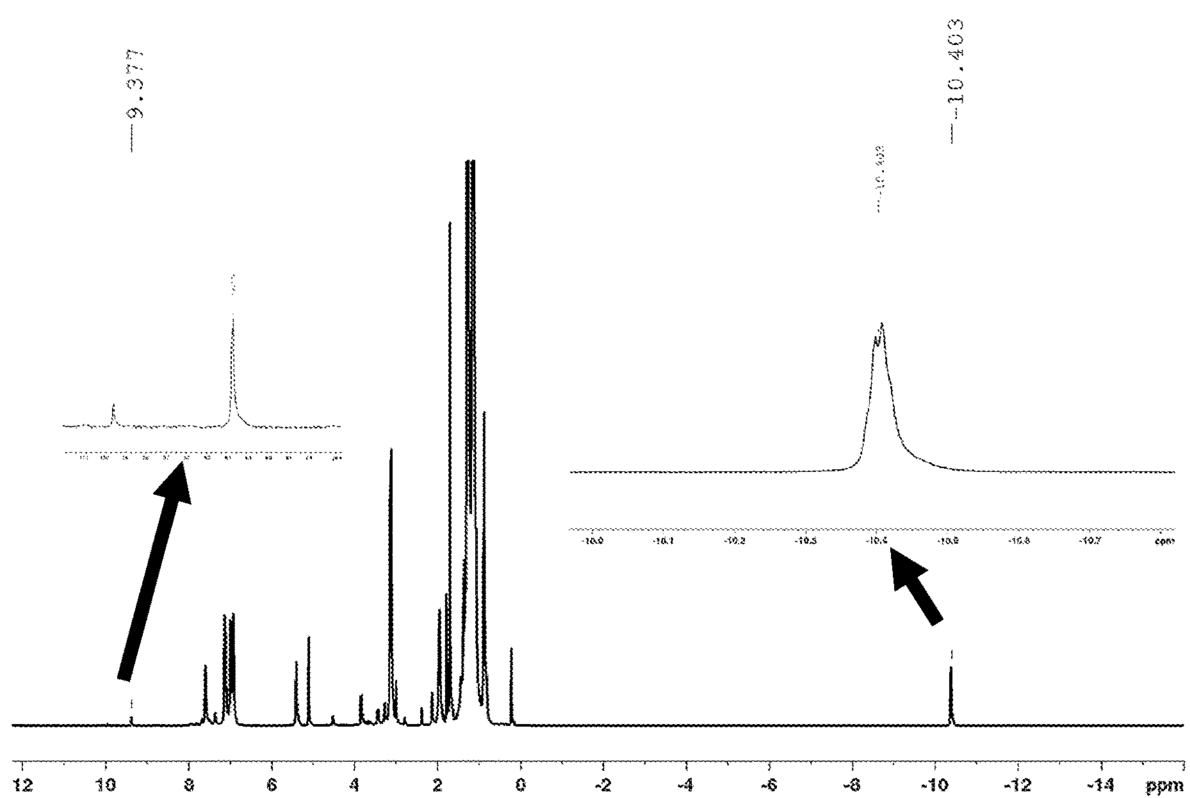
FIG. 6: High pressure $^{1}H$ NMR spectrum of metal complex of formula (II) at higher temperature in the presence of substrate S1.

FIG. 6 depicts high pressure $^1$H NMR spectrum of metal complex of formula (II) at higher temperature in the presence of substrate.

Figure 7:
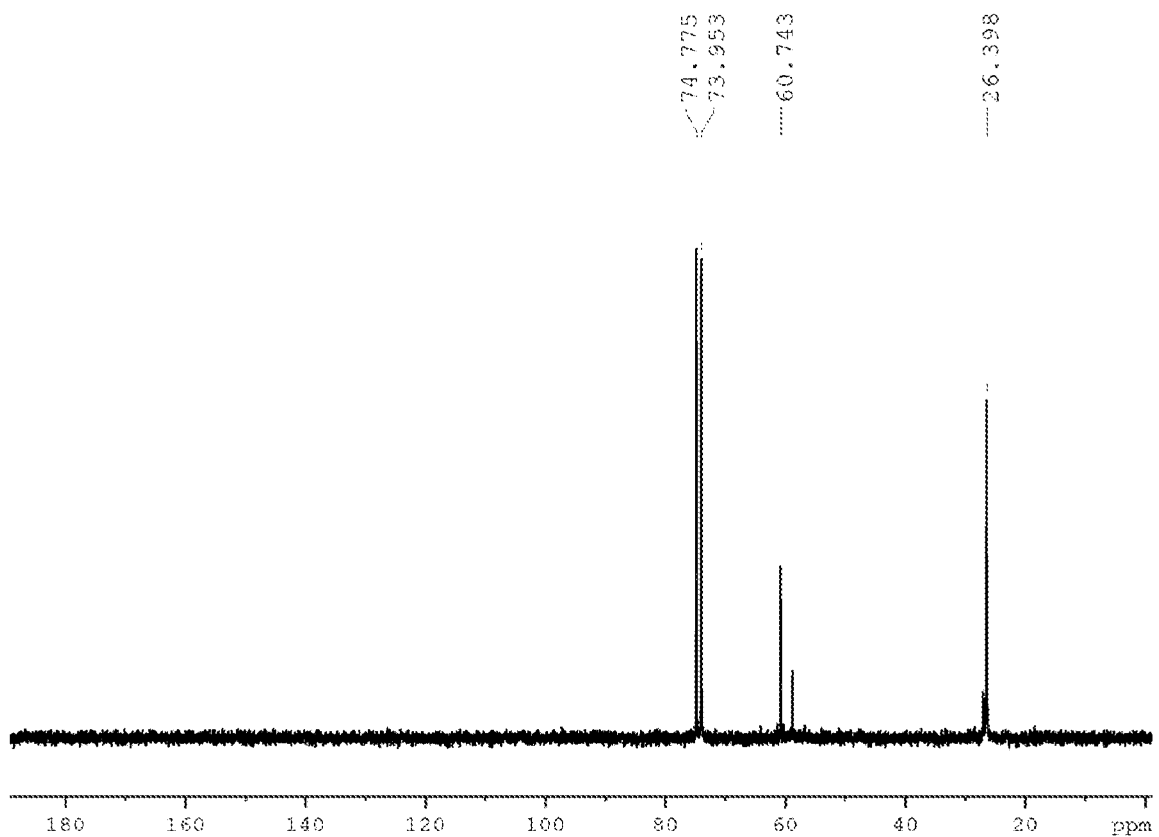
FIG. 7: High pressure $^{31}P$ NMR spectrum of metal complex of formula (II) at higher temperature in the presence of substrate S1.

FIG. 7 depicts high pressure $^{31}$P NMR spectrum of metal complex of formula (II) at higher temperature in the presence of substrate.

EXAMPLES

Following examples are given by way of illustration therefore should not be construed to limit the scope of the invention.

Example 1: Process for Preparation of (E)-3-(pentadec-8-1-yl)phenol (S1)

In case of CNSL, started with the technical CNSL which was a mixture of anacardic acid, cardanol, cardol and 2-methyl-cardol in smaller quantities. Decarboxylation of this mixture followed by vacuum distillation at 140° C. resulted in isolation of cardanol from the above mixture. Obtained cardanol was analyzed by $^1$H NMR spectroscopy and relative composition of monoene, diene and triene in cardanol was analyzed using HPLC.

Cardanol was selectively hydrogenated to monoene according to the literature report. Synthesis of monoene was carried out in a schlenk flask under inert conditions using argon atmosphere. In a typical experiment schlenk flask was charged with cardanol (18.6 g, 0.0623 mol) and catalyst (0.61 g, 0.0029 mol). Next, dry isopropanol (30 ml) was added to it. After this the reaction mixture was allowed to reflux at 90° C. for 18 hours under argon atmosphere. After 18 hours, the reaction mixture was allowed to cool to room temperature and solvents were removed in vacuuo. Next, Dichloromethane was added to the residue and it was filtered through silica. The filtrate was evaporated to get monoene S1. It was further analyzed using $^1$H NMR.

Example 2: Process for Preparation of 16-3(hydroxyphenyl) hexadecanal (P1)

In a typical hydroformylation experiment a stainless steel autoclave (450 mL) equipped with pressure regulator and a safety valve was employed. In a glove box the vials were charged with $[Rh(acac)(CO)_2]$ (0.002 g, 1 eq.), ligand L1 (0.0061 g, 2 eq.), solvent (1 ml), substrate (100 eq.) along with Teflon stirring bars. Before starting the catalytic reactions, the charged autoclave was purged three times with syngas ($CO:H_2$=1:1) and then pressurized to the desired pressure (see table 1). After catalysis, the autoclave was cooled to 0° C., and excess gas was vented. The conversion and regioselectivity were determined by $^1$H NMR spectroscopy using dibromomethane as an internal standard.

Optimization Studies:

a) Screening of Various Ligands:

The studies started with ligand screening and tested the activity of various ligands which suggested 1,2-DTBPMB ligand (L1) as a ligand of choice (Table 1).

TABLE 1

| Sr. No | Substrate | Ligand | L/M ratio | Temperature (° C.) | Pressure (bar) | Reaction time (hrs.) | Conversion (%) | L:B Selectivity |
|---|---|---|---|---|---|---|---|---|
| 01. | Monoene | L1 | 2 | 120 | 2.5 | 16 | 83 | 16:84 |
| 02. | Monoene | L2 | 2 | 120 | 2.5 | 16 | 61 | No linear |
| 03. | Monoene | L3 | 2 | 120 | 2.5 | 16 | 53 | 6:94 |
| 04. | Monoene | L4 | 2 | 125 | 1 | 18 | 5 | No linear |

Various other parameters such as temperature, pressure, reaction time and solvent to get the best selectivity towards the terminal product are screened. Solvent screening experiment supported the use of 1,4-dioxane as solvent. Although the selectivity for terminal aldehyde is better in p-xylene & mesitylene entries but overall conversion to aldehydes was less as compared to that in toluene and 1,4-dioxane (entries 2&3 vs. 1&6, Table 2). Formation of terminal aldehyde was not observed in case of NMP (entry 4) while in case of DME, selectivity for terminal aldehyde was 14% (entry 5). Therefore 1,4-dioxane was used as a solvent of choice for the rest of the isomerizing hydroformylation experiments.

b) Screening of Various Solvents:

Table 2 shows isomerizing hydroformylation of S1 and solvent screening.

TABLE 2

| Sr. No | Substrate | Solvent | L/M ratio | S/M ratio | Temp. (° C.) | Press. (Bar) | Reaction time (hrs.) | Conversion (%) | L:B Selectivity |
|---|---|---|---|---|---|---|---|---|---|
| 01. | Monoene | Toluene | 2 | 100 | 125 | 2 | 16 | 22 | 17:83 |
| 02. | Monoene | p-xylene | 2 | 100 | 125 | 2 | 16 | 59 | 20:80 |
| 03. | Monoene | Mesitylene | 2 | 100 | 125 | 2 | 16 | 50 | 20:80 |
| 04. | Monoene | NMP | 2 | 100 | 125 | 2 | 16 | 27 | No linear |
| 05. | Monoene | DME | 2 | 100 | 125 | 2 | 16 | 26 | 14:86 |
| 06. | Monoene | 1,4-dioxane | 2 | 100 | 125 | 2 | 16 | 44 | 20:80 |

c) Isomerizing HF of Monoene (S1) Using [Rh(Acac)$(CO)_2$] as Metal Precursor:

Table 3 shows isomerizing HF of monoene (S1) using [Rh(acac)$(CO)_2$] as metal precursor.

TABLE 3

| Run | Metal Precursor | L/M ratio | S/M ratio | T (° C.) | P (bar) | Reaction time (hrs) | Conversion (%) | l:b selectivity |
|---|---|---|---|---|---|---|---|---|
| 1 | [Rh(acac)$(CO)_2$] | 2 | 100 | 120 | 1 | 16 | 16 | 20:80 |
| 2. | [Rh(acac)$(CO)_2$] | 2 | 100 | 120 | 1 | 48 | 89 | 16:84 |
| 3. | [Rh(acac)$(CO)_2$] | 2 | 100 | 125 | 2 | 16 | 44 | 20:80 |
| 4. | [Rh(acac)$(CO)_2$] | 2 | 50 | 125 | 2 | 16 | 86 | 14:86 |
| 5. | [Rh(acac)$(CO)_2$] | 2 | 100 | 125 | 5 | 4 | 48 | 15:85 |
| 6. | [Rh(acac)$(CO)_2$] | 2 | 100 | 120 | 5 | 12 | 83 | 15:85 |
| 7. | [Rh(acac)$(CO)_2$] | 2 | 100 | 125 | 10 | 4 | 99 | 14:86 |
| 8. | [Rh(acac)$(CO)_2$] | 2 | 100 | 125 | 10 | 4 | 40 | No linear |
| 9. | [Rh(acac)$(CO)_2$] | 2 | 100 | 125 | 10 | 7 | 26 | 12:88 |
| 10. | [Rh(acac)$(CO)_2$] | 2 | 100 | 125 | 15 | 4 | 99 | 12:88 |
| 11. | [Rh(acac)$(CO)_2$] | 2 | 100 | 125 | 15 | 4 | 99 | 12:88 |
| 12. | [Rh(acac)$(CO)_2$] | 2 | 100 | 125 | 20 | 4 | 99 | 10:90 |
| 13. | [Rh(acac)$(CO)_2$] | 2 | 100 | 125 | 20 | 4 | 99 | 11:89 |
| 14. | [Rh(acac)$(CO)_2$] | 2 | 100 | 125 | 1 | 18 | 31 | 25:75 |
| 15. | [Rh(acac)$(CO)_2$] | 2 | 50 | 125 | 1 | 18 | 28 | 33:67 |
| 16. | [Rh(acac)$(CO)_2$] | 1 | 100 | 125 | 1 | 18 | 18 | 22:78 |
| 17. | [Rh(acac)$(CO)_2$] | 1.5 | 100 | 125 | 1 | 18 | 34 | 18:82 |
| 18. | [Rh(acac)$(CO)_2$] | 1 | 200 | 125 | 1 | 18 | 8 | 24:76 |
| 19. | [Rh(acac)$(CO)_2$] | 2 | 200 | 125 | 1 | 18 | 10 | 22:78 |
| 20. | [Rh(acac)$(CO)_2$] | 2 | 100 | 125 | 1 | 48 | 95 | 12:88 |
| 21. | [Rh(acac)$(CO)_2$] | 2 | 50 | 120 | 2 | 48 | 95 | 2:98 |
| 22. | [Rh(acac)$(CO)_2$] | 2 | 20 | 120 | 2 | 48 | 99 | No linear |

Example 3: Synthesis of monoene (E)-1-methoxy-3-(pentadec-8-en-1-yl) benzene (S2)

Compound S2 was synthesized by following a known literature procedure. Monoene (9.3 g, 0.0307 mol) and potassium carbonate (8.49 g, 0.0614 mol) were suspended in dry acetone. Methyl iodide (3.83 ml, 0.0614 mol) was added dropwise under inert conditions and reaction mixture was allowed to reflux at 60° C. for 6 h. The reaction was then cooled to 28-30° C. and the solvent was removed under reduced pressure to get white colored residue. The residue was dissolved in ethyl acetate. Now organic layer was washed with water (3*50 ml), dried over $MgSO_4$, filtered and evaporated to get yellow oil. The oil was further purified over a silica column using hexane-EtOAc (5:1) as eluents.

Example 4: Isomerizing Hydroformylation of Methyl Oleate

It is well known that the ligand coordination influences the regioselectivity in a hydroformylation reaction. A bis-equatorial coordination of ligand L2 around Rh metal centre with the help of high pressure $^{1}H$ and $^{31}P$ NMR spectroscopy is established. After establishing the coordination behavior of ligand L2, this ligand is employed for isomerizing hydroformylation of methyl oleate (MO).

Hydroformylation experiment a stainless steel autoclave (450 mL) equipped with pressure regulator and a safety valve was employed. In a glove box the vials were charged with $[Rh(acac)(CO)_2]$ (0.002 g, 1 eq.), ligand L2 (0.0114 g, 2 eq.), solvent (1 ml), substrate (100 eq.) along with Teflon stirring bars. Before starting the catalytic reactions, the charged autoclave was purged three times with syngas Scheme 4: Synthesis of Me-protected monoene

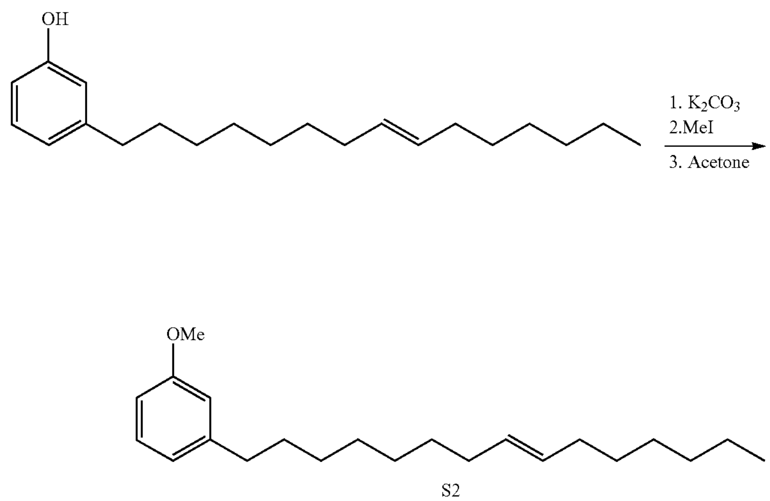

Table 4 shows Isomerizing HF of Me-protected monoene S1-Me.

TABLE 4

| Run | Metal Precursor | L/M ratio | S/M ratio | T (° C.) | P (bar) | Reaction time (hrs) | Conversion (%) | l:b selectivity |
|---|---|---|---|---|---|---|---|---|
| 1. | $[Rh(acac)(CO)_2]$ | 2 | 100 | 120 | 2 | 36 | 23 | 18:82 |
| 2. | $[Rh(acac)(CO)_2]$ | 2 | 50 | 120 | 2 | 48 | 34 | 16:84 |
| 3. | $[Rh(acac)(CO)_2]$ | 2 | 20 | 120 | 2 | 48 | 99 | No linear |
| 4. | $[Rh(acac)(CO)_2]$ 1,4-dioxane | 2 | 100 | 120 | 5 | 40 | 42 | 9:91 |
| 5. | $[Rh(acac)(CO)_2]$ MeOH | 2 | 100 | 120 | 5 | 40 | No Reaction | — |
| 6. | $[Rh(acac)(CO)_2]$ | 2 | 100 | 125 | 1 | 18 | 17 | 50:50 |
| 7. | $[Rh(acac)(CO)_2]$ | 1.5 | 100 | 120 | 1 | 18 | 19 | 28:72 |

($CO:H_2$=1:1) and then pressurized to the desired pressure (see table 5). After catalysis, the autoclave was cooled to 0° C., and excess gas was vented. The conversion and regioselectivity were determined by $^1H$ NMR spectroscopy and GC respectively.

Scheme 5: Isomerizing hydroformylation ofmethyl oleate

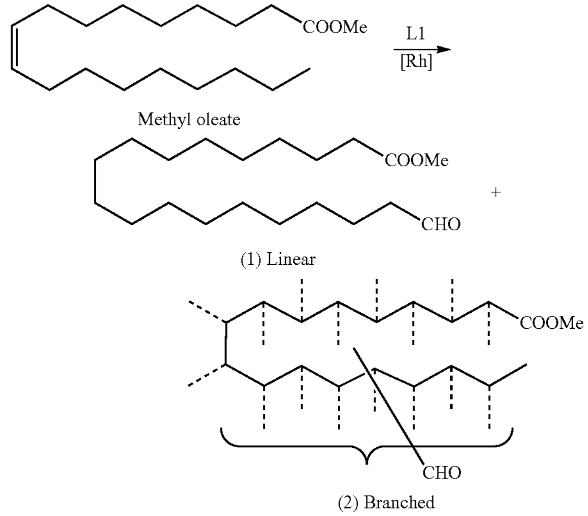

Table 5 shows Isomerizing hydroformylation of methyl oleate.

TABLE 5

| Run | Sub. | L:M | Ligand | Solvent | Temp (° C.) | Syngas (bars) | Time (h) | Conv. % | L:B |
|---|---|---|---|---|---|---|---|---|---|
| 1 | MO | 2 | L2 | Tol. | 120 | 2.5 | 16 | 47 | 15:85 |
| 2 | MO | 2 | L2 | Diox. | 120 | 2.5 | 16 | 40 | 18:82 |
| 3 | MO | 2 | L2 | Diox. | 120 | 5 | 16 | 77 | 18:82 |
| 4 | MO | 2 | L2 | Diox. | 120 | 1 | 16 | 20 | 43:57 |
| 5 | MO | 2 | L2 | Diox. | 120 | 1 | 48 | 32 | 75:25 |
| 6 | MO | 2 | L1 | Diox. | 120 | 2.5 | 16 | 73 | 6:94 |
| 7 | MO | 2 | L1 | Diox. | 120 | 1 | 16 | 29 | 10:90 |

Sub. = substrate,

S/M = 100,

MO = Methyl oleate,

Example 5: Reaction of $[Rh(acac)(CO)_2]$ and Ligand L1

$[Rh(acac)(CO)_2]$ (0.020 g, 0.000077 mol) and ligand L1 (0.030 g, 0.000077 mol) were dissolved in dry toluene-$d_8$ (0.3 ml) under inert conditions. This mixture was mixed properly to get a clear solution. Next, the reaction mixture was transferred to a high pressure NMR tube. The tube was degassed using freeze-pump-thaw cycles. Next, the NMR tube was purged 2-3 times with syngas and then pressurized to 10 bars. Now the reaction mixture was analyzed using time resolved high pressure, high temperature $^1H$ and $^{31}P$ NMR spectroscopy. The bisphosphine ligand can coordinate around trigonal bipyramidal Rh centre in two different modes: axial-equatorial (C1) or equatorial-equatorial (C2) or both the species may be in equilibrium.

Scheme 6

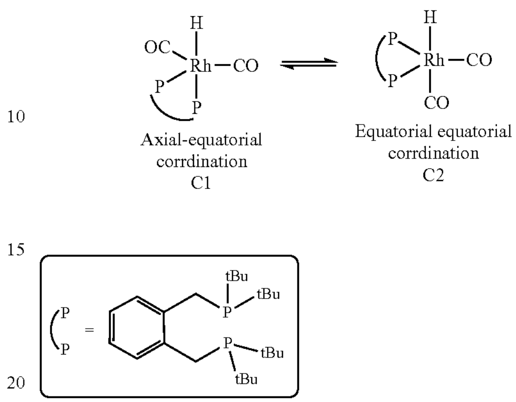

When NMR spectrum was recorded right after pressurizing, the hydride signal was not observed. However it started appearing within half an hour. It was clearly visible within one hour. The intensity of hydride signal was improved at higher temperature and at 70° C. a hydride signal was split into a doublet possibly due to coupling with Rh metal. This suggests the equatorial-equatorial coordination (C2) of ligand around Rh. This was further confirmed by high temperature $^{31}P$ NMR spectroscopy that showed a doublet at 74 ppm at 70° C. which indicated the exclusive formation of bis-equatorially coordinated Rh complex. Free ligand was not observed at 90° C. These experimental evidence suggested formation of C2 as the catalyst that catalyzes the hydroformylation of CNSL.

Example 6: Reduction of Diolefinic Monoaldehyde (P6) to P8

The hydrogenation of alkenes containing aldehyde group is known in literature. Similar procedure with slight modification was followed to reduce P6. Thus, subsequent reduction of monoaldehyde P6 using Pd/C led to the formation of AA type monomer P8 (Scheme 4) with excellent conversion.

Scheme 7: Subsequent reduction of diolefinic monoaldehyde P6 to P8.

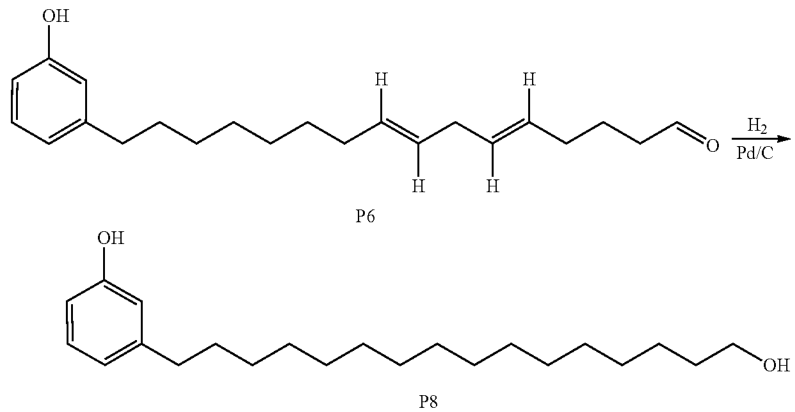

P6 (0.020 g) and palladium on charcoal (0.025 g) were taken in a RB flask and dry methanol (5 ml) was added to it. After the desired reaction time, the reaction mixture was filtered through a pad of celite and washed with DCM. Obtained filtrate was evaporated in vacuuo to get white colored solid (0.018 g, 89%). Details of optimization studies are summarized in table 6.

TABLE 6

| S. No. | Solvent | Temperature (° C.) | $H_2$ Pressure (bar) | Reaction time (hrs.) | Conversion (%) |
|---|---|---|---|---|---|
| 01 | MeOH | 28 | 2 | 18 | 37 |
| 02 | MeOH | 50 | 10 | 5 | 85 |
| 03 | MeOH | 50 | 10 | 12 | >99 |

$^1$H NMR (500 MHz, $CDCl_3$, 298K): δ=7.14 (t, $J_{H-H}$=7 Hz, 1H, $H_f$), 6.76 (d, $J_{H-H}$=7.3 Hz, 1H, $H_g$), 6.66 (m, 2H, $H_g$), 4.38 (t, $J_{H-H}$=4.5 Hz, 1H, $H_a$), 3.34 (m, 2H, $H_b$), 2.57 (t, $J_{H-H}$=7 Hz, 2H, $H_h$), 1.60 (m, 6H, $H_c$), 1.26 (m, 22H, $H_j$). $^{13}$C NMR (125 MHz, $CDCl_3$, 298K): δ=157.2 ($C_e$), 145.1 ($C_k$), 129.5 ($C_f$), 121.1 ($C_g$), 115.4 ($C_g$), 112.6 ($C_g$), 58.7 ($C_b$), 36.7 ($C_h$), 32.1 ($C_c$), 29.8 ($C_j$), 26.3 ($C_j$). ESI-MS (+ve mode): m/z=335.29 [M+H]+.

Example 7: Preparation, Separation and Characterization of Linear Aldehyde 0.48 g of Me-protected monoene was hydroformylated at 125° C., 2 bar syngas pressure for 24 hours with 2 mol % {[Rh(acac)$(CO)_2$]=4 mg} catalyst loading. As calculated by $^1$H NMR, a total conversion of 64% was obtained with 46% aldehyde. After the reaction, the linear aldehyde was separated from the reaction mixture using flash silica column chromatography with hexane and diethyl ether (100:1 to 10:1) as eluents. The linear aldehyde was isolated in 10% yield as per following method.

316.52 g of Me-protected monoene (S2) gives 346.55 g of aldehydes (P1' & P2').

0.48 g Me-protected monoene (S2) should give (346.55*0.48)/316.52=0.52 g (P1' & P2').

Considering the total conversion of 64% (64*0.52 g)/100=0.33 g (P1' & P2')

Since conversion to aldehyde is 46%, (0.33 g*46)/100=0.15 g (P1' & P2') should be obtained.

After column 0.015 g of P1' was isolated.

Therefore, isolated % yield of P1'=(0.015 g/0.15 g)/100=10%.

$^1$H NMR (500 MHz, $CDCl_3$, 298K): δ=9.77 (t, 1H, $H_a$), 7.20 (t, 1H, $H_f$), 6.77 (m, 3H, $H_g$), 3.81 (s, 3H, $H_d$), 2.58 (t, 2H, $H_h$), 2.38 (m, 2H, $H_b$), 1.58 (m, 6H, $H_c$), 1.26 (m, 20H, $H_j$). $^{13}$C NMR (125 MHz, $CDCl_3$, 298K): δ=203.2 (Ca), 159.9 ($C_e$), 144.6 ($C_k$), 129.4 ($C_f$), 121.0 ($C_g$), 114.4 ($C_g$), 111.0 ($C_g$), 55.3 ($C_d$), 44.1 ($C_b$), 36.2 ($C_h$), 32.3 ($C_c$), 31.6 ($C_c$), 29.9-29.6 ($C_j$), 26.2 ($C_j$). ESI-MS (+ve mode): m/z=347.29 $[M+H]^+$.

Example 8: Control Experiments

A. Hydroformylation of conjugated diene:

Procedure: In a typical isomerizing-hydroformylation experiment a stainless steel autoclave (450 mL) equipped with pressure regulator and a safety valve was used. Individual vials were charged with metal precursor (0.002 g), ligand (0.0061 g), solvent (1 ml), 1,3-butadiene (0.21 ml, 100 eq.) and stirring bars in a glove box. The vials were transferred to autoclave and the autoclave was purged three times with syngas ($CO:H_2$=1:1) before pressurizing it to the desired pressure. The autoclave was heated at 100° C. at 1 bar syngas pressure for 16 hours. After completion of reaction, the autoclave was cooled to 0° C., and excess gas was vented off in a well-ventilated fume-hood. The conversion and regioselectivity were determined by $^1$H NMR spectroscopy using dibromomethane as an internal standard.

Example 9: One Pot Isomerization-Hydroformylation-Hydrogenation

A tandem one pot isomerization-hydroformylation-hydrogenation sequence was attempted and the results are presented in table 7. Substrate (S3) CNSL-Cardanol as chosen as the representative substrate and an I-HF experiment was performed in presence of Pd/C (0.020 g) with a $CO:H_2$ ratio of 1:4 (table 7, run 1). As evident, although 68% conversion was observed, the conversion to aldehyde was negligible (only 1%). This indicates that hydrogenation become the dominant reaction and suppress hydroformylation.

TABLE 7

| Run | Substrate | T (° C.) | P (bar) | CO:$H_2$ | T (hrs) | Conversion (%) |
|---|---|---|---|---|---|---|
| 1 | CNSLcardanol | 120 | 4 | 1:4 | 16 | 68 (1) |

[Rh] = [Rh(acac)$(CO)_2$] (2 mg), L/M = 2, solvent = 1,4-dioxane, total conversion was determined by $^1$H NMR spectroscopy using $CH_2Br_2$ as an internal standard.

Example 10: Reaction of [Rh(Acac)$(CO)_2$], Ligand L1 in Presence of Substrate

[Rh(acac)$(CO)_2$] (0.030 g, 0.000116 mol) and ligand L1 (0.092 g, 0.000232 mol) were dissolved in dry toluene-$d_8$ (0.3 ml) under inert conditions. This mixture was mixed properly to get a clear solution. Next, trans-4-octene (0.018 ml, 0.000116) was added to the above solution and the reaction mixture was transferred to a high pressure NMR tube. The tube was degassed using freeze-pump-thaw cycles. Next, the NMR tube was purged 2-3 times with syngas and then pressurized to 10 bars. The tube was heated at 90° C. for 4 hours. After 4 hours the reaction mixture was analyzed using high pressure and high temperature $^1$H and $^{31}$P NMR spectroscopy at 90° C. The high-pressure $^{31}$P NMR spectrum of this solution at 90° C. revealed a doublet centered at 74.2 ppm with a $^1J_{Rh-P}$ coupling constant of 135 Hz. The corresponding proton NMR of this solution displayed a broad doublet centered at −10.35 ppm with $J_{P-H}$/$J_{Rh-H}$ coupling constant of <3.5 Hz. A doublet in the $^{31}$P NMR spectrum and a fairly small $J_{P-H}$ is a characteristic of a predominantly equatorial-equatorial (ee) coordination mode of the two phosphorus donors.

Example 11: Isomerizing Hydroformylation of Cashew Nut Shell Liquid and Short Chain Internal Olefins Table 8 gives Isomerizing hydroformylation of cashew nut shell liquid and short chain internal olefins[a].

TABLE 8

| Run | Subs[b] | T (° C.) | P (bar) | T (hrs) | Conversion[c] (%) | l:b selectivity |
|---|---|---|---|---|---|---|
| 1 | S1(1) | 120 | 1 | 16 | 16 (7) | 20:80 |
| 2 | S1(1) | 125 | 2 | 16 | 44 (20) | 20:80 |
| 3 | S1(1) | 120 | 5 | 12 | 83 (30) | 15:85 |
| 4 | S1(1) | 125 | 10 | 4 | 99 (42) | 14:86 |
| 5 | S1(1) | 125 | 15 | 4 | 99 (63) | 12:88 |
| 6 | S1(1) | 125 | 20 | 4 | 99 (88) | 10:90 |
| 7 | S1(1) | 125 | 1 | 18 | 33 (22) | 28:72 |
| 8 | S1(1) | 120 | 1 | 48 | 89 (80) | 16:84 |
| 9 | S1(1) | 120 | 2 | 36 | 38 (37) | 14:86 |
| 10 | S2(1) | 120 | 2 | 36 | 56 (37) | 18:82 |
| 11 | S2(1) | 125 | 1 | 18 | 17 (12) | 50:50 |
| 12 | S2(1) | 120 | 5 | 40 | 51 (50) | 9:91 |
| 13 | S3(2.5) | 125 | 1 | 18 | 74 (26) | 40:60 |
| 14 | S3(2.5) | 120 | 1 | 10 | 60 (27) | 52:48 |
| 15 | S3(2.5) | 120 | 1 | 5 | 53 (16) | 70:30 |
| 16 | S3(2.5) | 120 | 1 | 3 | 50 (18) | 74:26 |
| 17 | S4(2.5) | 120 | 1 | 10 | 70 (11) | 65:35 |
| 18 | S4(2.5) | 120 | 1 | 5 | 64 (9) | 68:32[b] |
| 19 | S4(2.5) | 120 | 1 | 3 | 64 (6) | 74:26 |
| 20 | S5(1) | 120 | 1 | 16 | 93 | 37:63 |
| 21* | S5(1) | 120 | 1 | 16 | 99 | 48:52 |
| 22 | S6(1) | 120 | 1 | 16 | 98 | 35:65 |
| 23* | S6(1) | 120 | 1 | 16 | 88 | 51:49 |

[a]Subs = substrates, S/M = 100, S1 = monoene, S2 = Me-protected monoene, S3 = CNSL-cardanol, S4 = Me protected CNSL-cardanol, S5 = cis-2-octene, S6 = trans-4-octene, [Rh] = [Rh(acac)$(CO)_2$] (2 mg), L/M = 2, solvent = 1,4-dioxane, total conversion and L/B selectivities determined by $^1$H NMR spectroscopy using $CH_2Br_2$ as an internal standard.

[b]The average number of double bonds in the substrate is mentioned in bracket.

[c]This was further confirmed by HPLC, the number in the bracket indicate conversion to aldehyde out of the total conversion.

[d]These experiments were performed in duplicate, and the L/B ratio was determined by taking the average of two experiments.

*Indicates that L1 was used as a ligand.

Example 12: Isomerizing Hydroformylation of S3 to P1 and P6

Isomerizing hydroformylation of CNSL-cardanol was attempted using optimized conditions and led to the production of a mixture of aldehydes P3-P7 along with various branched isomers. The terminal selectivity was determined by proton NMR using dibromomethane as an internal standard. The NMR selectivities were further supported by HPLC. The major terminal aldehydes P1 and P6 were separated by column chromatography (petroleum ether:ethyl acetate, 90:10) and P6 (44% isolated yield) was fully characterized. HPLC analyses were performed on Agilent 1260 infinity series instrument using ACN+water+formic acid (93+2+5) as eluents, flow rate 0.5 ml/min., column C18, 5 μm, 4.6*250 mm, λmax=273 nm; Rt=6.3 min.

Advantages of the Present Invention

- An unprecedented terminal selectivity of 50% is observed in case of S1Me and selectivity of 75% is observed in case of methyl Oleate.
- The bifunctional molecules obtained via isomerizing hydroformylation of CNSL and methyl oleate have been isolated and converted to potential hydroxy acid AB type monomers. Thus, Cashew Nut Shell Liquid was converted to useful feedstock chemicals and monomers.

We claim:

1. A compound of formula (I), wherein;

Formula (I)

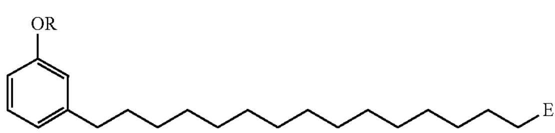

R is hydrogen or alkyl; and

E is selected from —C(O)H, —$CH_2$OH, and —OH.

2. The compound according to claim 1, wherein the compound is 16-(3-hydroxyphenyl) hexadecanal or 16-(3-methoxyphenyl) hexadecanal.

* * * * *